(12) United States Patent
Johlic et al.

(10) Patent No.: US 10,255,906 B2
(45) Date of Patent: Apr. 9, 2019

(54) SENSORS AND ANALYTICS FOR READING COMPREHENSION

(71) Applicant: International Business Machines Corporation, Armonk, NY (US)

(72) Inventors: Marc K. Johlic, Seminole, FL (US); Susann M. Keohane, Austin, TX (US); Emi K. Olsson, Germantown, NY (US)

(73) Assignee: International Business Machines Corporation, Armonk, NY (US)

( * ) Notice: Subject to any disclaimer, the term of this patent is extended or adjusted under 35 U.S.C. 154(b) by 128 days.

(21) Appl. No.: 15/378,470

(22) Filed: Dec. 14, 2016

(65) Prior Publication Data
US 2018/0160963 A1    Jun. 14, 2018

(51) Int. Cl.
| G10L 15/00 | (2013.01) |
| A61B 5/00 | (2006.01) |
| G09B 17/00 | (2006.01) |
| G10L 13/00 | (2006.01) |
| G10L 17/00 | (2013.01) |
| G09B 5/06 | (2006.01) |
| A61B 5/04 | (2006.01) |
| A61B 5/16 | (2006.01) |

(52) U.S. Cl.
CPC .......... *G10L 15/00* (2013.01); *A61B 5/04001* (2013.01); *A61B 5/16* (2013.01); *A61B 5/4088* (2013.01); *A61B 5/6822* (2013.01); *G09B 5/06* (2013.01); *G09B 17/003* (2013.01); *G10L 13/00* (2013.01); *G10L 17/00* (2013.01); *A61B 5/4803* (2013.01)

(58) Field of Classification Search
None
See application file for complete search history.

(56) References Cited

U.S. PATENT DOCUMENTS

| 3,368,551 A | 2/1968 | Hardyck |
| 5,899,972 A * | 5/1999 | Miyazawa ............... G10L 15/22 704/249 |
| 9,101,279 B2 | 8/2015 | Ritchey et al. |
| 2007/0106501 A1 | 5/2007 | Morita et al. |
| 2008/0010071 A1* | 1/2008 | Callahan ................. G10L 15/24 704/270 |

(Continued)

FOREIGN PATENT DOCUMENTS

| CN | 102999154 | 3/2013 |
| CN | 103294199 | 9/2013 |

OTHER PUBLICATIONS

Katamaya, "Invention Awards: A Real-Life Babel Fish for the Speaking Impaired," Popular Science, May 2009, 3 pages.

(Continued)

Primary Examiner — Jason T Yen
(74) Attorney, Agent, or Firm — VanLeeuwen & VanLeeuwen; Mercedes L. Hobson

(57) ABSTRACT

An approach is provided that receives, from a neurological sensor worn by a user, words as they are silently read the user. The words being read by the user correspond to a set of actual words that are included in a passage that is being read by the user. The approach compares the words as read by the user with the actual words included in the passage to identify one or more reading mistakes. The reading mistakes are analyzed resulting in a set of feedback that is provided to the user.

12 Claims, 5 Drawing Sheets

(56) References Cited

U.S. PATENT DOCUMENTS

| | | | |
|---|---|---|---|
| 2012/0113209 A1* | 5/2012 | Ritchey | H04N 5/2254 |
| | | | 348/14.02 |
| 2013/0227421 A1* | 8/2013 | Burgess | G09B 17/003 |
| | | | 715/738 |
| 2015/0095036 A1* | 4/2015 | Zilberman | G10L 15/20 |
| | | | 704/275 |
| 2015/0338917 A1 | 11/2015 | Steiner et al. | |

OTHER PUBLICATIONS

Wren, "The Cognitive Foundations of Learning to Read: A Framework," Southwest Educational Development Laboratory, 2001, 62 pages.

"How to Improve Reading Speend by Eliminating Subvocalization," Spreeder, eReflect Software, Aug. 2010, 9 pages.

Daneman et al., Assessing the importance of subvocalization during normal silent reading, Abstract, Reading and Writing, Springer Link, Mar. 1992, vol. 4, Issue 1, 4 pages.

"The Audeo by Ambient—Using voice as an input," Nerve, Sep. 2015, 4 pages.

* cited by examiner

SENSORS AND ANALYTICS FOR READING COMPREHENSION

BACKGROUND OF THE INVENTION

Description of Related Art

Companies and government invest heavily in Education. One of the pivotal moments in a person education is learning to read. It is estimated that one in five American children has trouble reading. It is even more challenging for students with who speak non-native language or who have a learning disabilities such as dyslexia or processing issues. These students often need to apply hard work and receive one-on-one assistance to overcome their challenges. A goal of modern society is to help these students be more independent in learning to read, and to assist teachers in quickly assessing the students' reading abilities and challenges.

SUMMARY

An approach is provided that receives, from a neurological sensor worn by a user, words as they are silently read the user. The words being read by the user correspond to a set of actual words that are included in a passage that is being read by the user. The approach compares the words as read by the user with the actual words included in the passage to identify one or more reading mistakes. The reading mistakes are analyzed resulting in a set of feedback that is provided to the user.

The foregoing is a summary and thus contains, by necessity, simplifications, generalizations, and omissions of detail; consequently, those skilled in the art will appreciate that the summary is illustrative only and is not intended to be in any way limiting. Other aspects, inventive features, and advantages of the present invention will be apparent in the non-limiting detailed description set forth below.

BRIEF DESCRIPTION OF THE DRAWINGS

The present invention may be better understood, and its numerous objects, features, and advantages made apparent to those skilled in the art by referencing the accompanying drawings, wherein.

DETAILED DESCRIPTION

Figure 1:
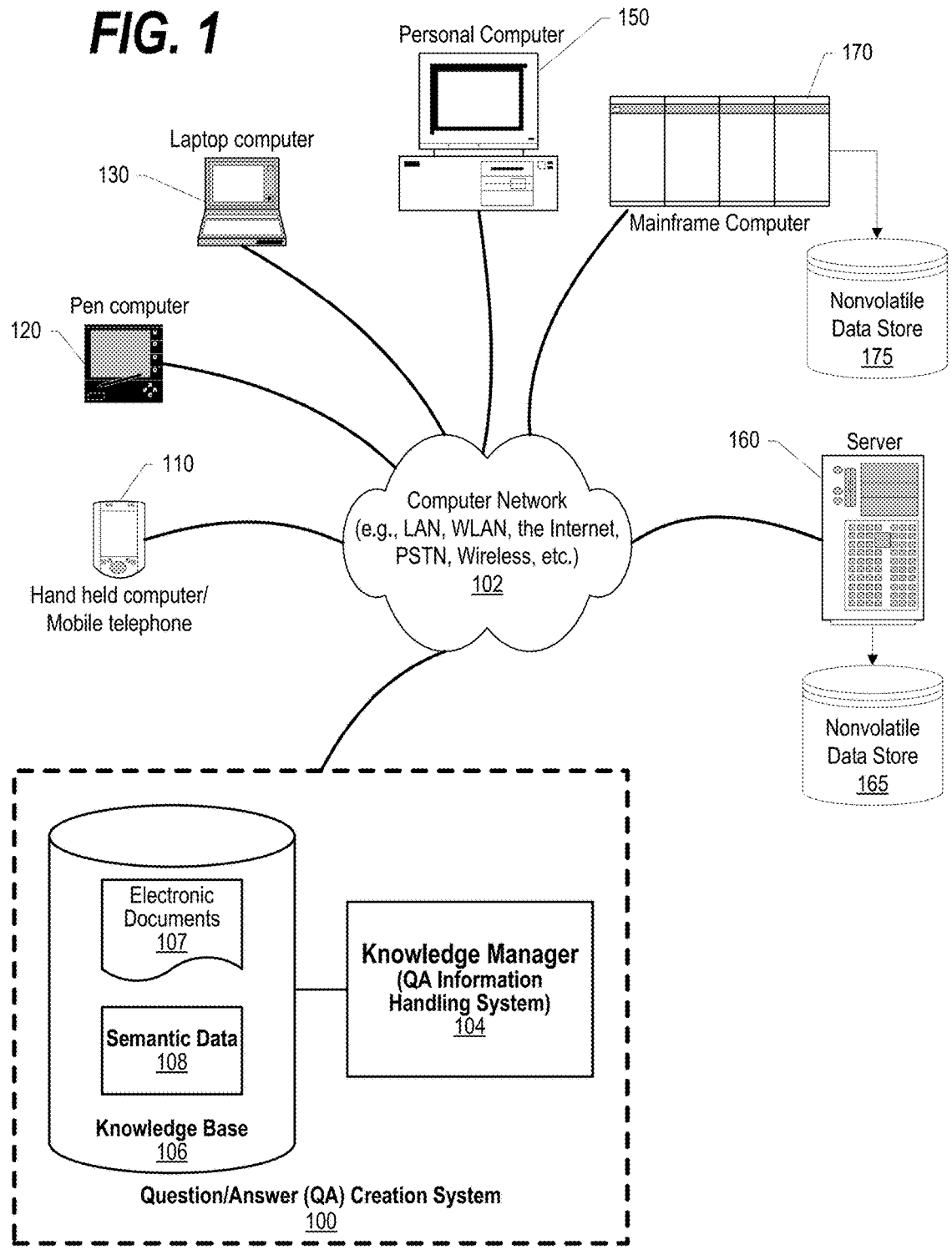
FIG. 1 depicts a network environment that includes a knowledge manager that utilizes a knowledge base.

FIGS. 1-5 describe an Enhance Reading Comprehension system. This system gathers the words the student reads and compares them to the words written on the page. With this information, we can use heuristics to capture patterns in the students reading (i.e. errors) and map it against known techniques that can enhance the students' reading abilities. Our technology records and monitors the student's performance using scientific data. It assists teachers in assisting the students who may need the most one-one help. This system may be of great benefit to non-vocal users, uses with reading disabilities, such as dyslexia, users with language processing disorders, and non-native language speakers.

The reading enhancement system works by performing a set of processes to assess a user's reading abilities and challenges. First, the system collects the words as read by the user from the neurological sensor that utilizes vocal sensor processing technology The system gathers the words as they are read by the user as the user is reading, out loud or silently, by leveraging sensor technology, such as The Audeo™ by Ambient Corporation. In one embodiment, the neurological sensor is based on the idea that neurological signals sent from the brain to the throat area to initiate speech, such as occur during reading, still travel to the throat area even if the user does not audibly speak the words. Thus, even when the user does not audibly speak the words, neurological signals that represent the intended speech exist when the user is reading. This is known as "sub-vocal speech," and is performed by humans whenever a person thinks of a word or sentence without saying it out loud, the person's brain still sends the signals to the person's mouth and throat. These signals are captured by the neurological sensor from which the system gathers the words as read by the user.

The approach also collects the actual words from the passage that is being read by the user. The words as read by the user are then compared with the actual words from the passage and analyzed to reveal mistakes made by the user while reading. From these mistakes, the approach detects reading patterns and cross-reference the patterns to known reading comprehension research or learning disabilities, such as dyslexia. The identification of patterns and possible learning, or reading, disabilities can be used by teachers or others assisting the user to offer reading techniques to improve the student's reading. The system stores the user's historical data to track and monitor progress. In one embodiment, the approach performs analytics on a cohort of individuals to help identify predictive patterns. In a further embodiment, a question-answering (QA) system is used to match the user's patterns with currently known patterns. From mistakes made by the user, the system further identifies words with which the student is struggling. This might be due to the user being a non-native language reader or due to a reading disability, such as dyslexia, that can cause confusion between words. The system can further provide feedback that can include troublesome words as well as word pronunciation, definition of words, pictures of the word, or translations of the word to the user's native language, in the case of a non-native language reader.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

FIG. 1 depicts a schematic diagram of one illustrative embodiment of a question/answer creation (QA) system 100 in a computer network 102. QA system 100 may include a knowledge manager computing device 104 (comprising one or more processors and one or more memories, and potentially any other computing device elements generally known in the art including buses, storage devices, communication interfaces, and the like) that connects QA system 100 to the computer network 102. The network 102 may include multiple computing devices 104 in communication with each other and with other devices or components via one or more wired and/or wireless data communication links, where each communication link may comprise one or more of wires, routers, switches, transmitters, receivers, or the like. QA system 100 and network 102 may enable question/answer (QA) generation functionality for one or more content users. Other embodiments of QA system 100 may be used with components, systems, sub-systems, and/or devices other than those that are depicted herein.

QA system 100 may be configured to receive inputs from various sources. For example, QA system 100 may receive input from the network 102, a corpus of electronic documents 107 or other data, a content creator, content users, and other possible sources of input. In one embodiment, some or all of the inputs to QA system 100 may be routed through the network 102. The various computing devices on the network 102 may include access points for content creators and content users. Some of the computing devices may include devices for a database storing the corpus of data. The network 102 may include local network connections and remote connections in various embodiments, such that knowledge manager 100 may operate in environments of any size, including local and global, e.g., the Internet. Additionally, knowledge manager 100 serves as a front-end system that can make available a variety of knowledge extracted from or represented in documents, network-accessible sources and/or structured data sources. In this manner, some processes populate the knowledge manager with the knowledge manager also including input interfaces to receive knowledge requests and respond accordingly.

In one embodiment, the content creator creates content in electronic documents 107 for use as part of a corpus of data with QA system 100. Electronic documents 107 may include any file, text, article, or source of data for use in QA system 100. Content users may access QA system 100 via a network connection or an Internet connection to the network 102, and may input questions to QA system 100 that may be answered by the content in the corpus of data. As further described below, when a process evaluates a given section of a document for semantic content, the process can use a variety of conventions to query it from the knowledge manager. One convention is to send a well-formed question. Semantic content is content based on the relation between signifiers, such as words, phrases, signs, and symbols, and what they stand for, their denotation, or connotation. In other words, semantic content is content that interprets an expression, such as by using Natural Language (NL) Processing. Semantic data 108 is stored as part of the knowledge base 106. In one embodiment, the process sends well-formed questions (e.g., natural language questions, etc.) to the knowledge manager. QA system 100 may interpret the question and provide a response to the content user containing one or more answers to the question. In some embodiments, QA system 100 may provide a response to users in a ranked list of answers.

In some illustrative embodiments, QA system 100 may be the IBM Watson™ QA system available from International Business Machines Corporation of Armonk, N.Y., which is augmented with the mechanisms of the illustrative embodiments described hereafter. The IBM Watson™ knowledge manager system may receive an input question which it then parses to extract the major features of the question, that in turn are then used to formulate queries that are applied to the corpus of data. Based on the application of the queries to the corpus of data, a set of hypotheses, or candidate answers to the input question, are generated by looking across the corpus of data for portions of the corpus of data that have some potential for containing a valuable response to the input question.

The IBM Watson™ QA system then performs deep analysis on the language of the input question and the language used in each of the portions of the corpus of data found during the application of the queries using a variety of reasoning algorithms. There may be hundreds or even thousands of reasoning algorithms applied, each of which performs different analysis, e.g., comparisons, and generates a score. For example, some reasoning algorithms may look at the matching of terms and synonyms within the language of the input question and the found portions of the corpus of data. Other reasoning algorithms may look at temporal or spatial features in the language, while others may evaluate the source of the portion of the corpus of data and evaluate its veracity.

The scores obtained from the various reasoning algorithms indicate the extent to which the potential response is inferred by the input question based on the specific area of focus of that reasoning algorithm. Each resulting score is then weighted against a statistical model. The statistical model captures how well the reasoning algorithm performed at establishing the inference between two similar passages for a particular domain during the training period of the IBM Watson™ QA system. The statistical model may then be used to summarize a level of confidence that the IBM Watson™ QA system has regarding the evidence that the potential response, i.e. candidate answer, is inferred by the question. This process may be repeated for each of the candidate answers until the IBM Watson™ QA system identifies candidate answers that surface as being significantly stronger than others and thus, generates a final answer, or ranked set of answers, for the input question. More information about the IBM Watson™ QA system may be obtained, for example, from the IBM Corporation website, IBM Redbooks, and the like. For example, information about the IBM Watson™ QA system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

Types of information handling systems that can utilize QA system 100 range from small handheld devices, such as handheld computer/mobile telephone 110 to large mainframe systems, such as mainframe computer 170. Examples of handheld computer 110 include personal digital assistants (PDAs), personal entertainment devices, such as MP3 players, portable televisions, and compact disc players. Other examples of information handling systems include pen, or tablet, computer 120, laptop, or notebook, computer 130, personal computer system 150, and server 160. As shown, the various information handling systems can be networked together using computer network 102. Types of computer network 102 that can be used to interconnect the various information handling systems include Local Area Networks (LANs), Wireless Local Area Networks (WLANs), the Internet, the Public Switched Telephone Network (PSTN), other wireless networks, and any other network topology that can be used to interconnect the information handling systems. Many of the information handling systems include nonvolatile data stores, such as hard drives and/or nonvolatile memory. Some of the information handling systems shown in FIG. 1 depicts separate nonvolatile data stores (server 160 utilizes nonvolatile data store 165, and mainframe computer 170 utilizes nonvolatile data store 175. The nonvolatile data store can be a component that is external to the various information handling systems or can be internal to one of the information handling systems. An illustrative example of an information handling system showing an exemplary processor and various components commonly accessed by the processor is shown in FIG. 2.

Figure 2:
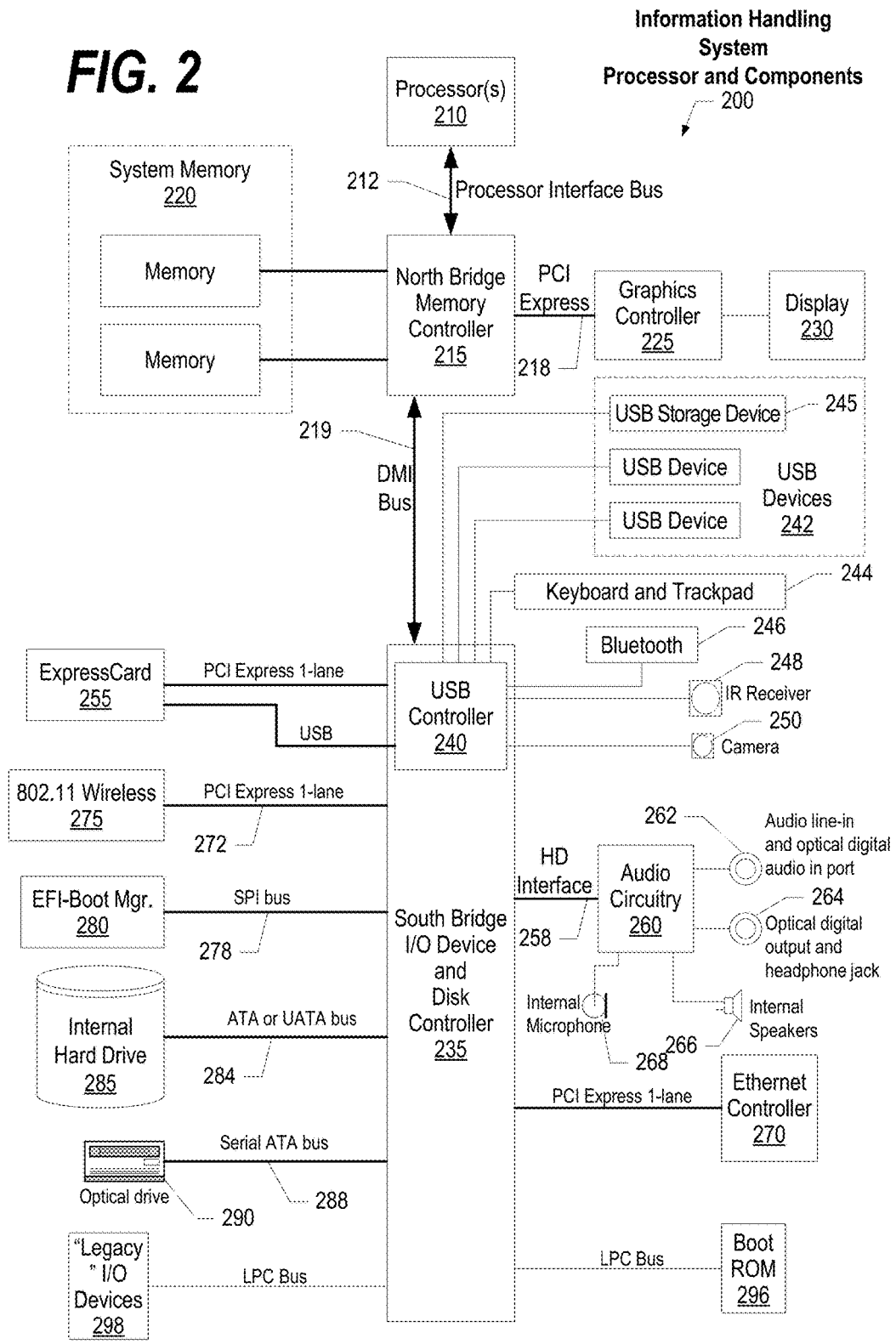
FIG. 2 is a block diagram of a processor and components of an information handling system such as those shown in FIG. 1.

FIG. 2 illustrates information handling system 200, more particularly, a processor and common components, which is a simplified example of a computer system capable of performing the computing operations described herein. Information handling system 200 includes one or more processors 210 coupled to processor interface bus 212. Processor interface bus 212 connects processors 210 to Northbridge 215, which is also known as the Memory Controller Hub (MCH). Northbridge 215 connects to system memory 220 and provides a means for processor(s) 210 to access the system memory. Graphics controller 225 also connects to Northbridge 215. In one embodiment, PCI Express bus 218 connects Northbridge 215 to graphics controller 225. Graphics controller 225 connects to display device 230, such as a computer monitor.

Northbridge 215 and Southbridge 235 connect to each other using bus 219. In one embodiment, the bus is a Direct Media Interface (DMI) bus that transfers data at high speeds in each direction between Northbridge 215 and Southbridge 235. In another embodiment, a Peripheral Component Interconnect (PCI) bus connects the Northbridge and the Southbridge. Southbridge 235, also known as the I/O Controller Hub (ICH) is a chip that generally implements capabilities that operate at slower speeds than the capabilities provided by the Northbridge. Southbridge 235 typically provides various busses used to connect various components. These busses include, for example, PCI and PCI Express busses, an ISA bus, a System Management Bus (SMBus or SMB), and/or a Low Pin Count (LPC) bus. The LPC bus often connects low-bandwidth devices, such as boot ROM 296 and "legacy" I/O devices (using a "super I/O" chip). The "legacy" I/O devices (298) can include, for example, serial and parallel ports, keyboard, mouse, and/or a floppy disk controller. The LPC bus also connects Southbridge 235 to Trusted Platform Module (TPM) 295. Other components often included in Southbridge 235 include a Direct Memory Access (DMA) controller, a Programmable Interrupt Controller (PIC), and a storage device controller, which connects Southbridge 235 to nonvolatile storage device 285, such as a hard disk drive, using bus 284.

ExpressCard 255 is a slot that connects hot-pluggable devices to the information handling system. ExpressCard 255 supports both PCI Express and USB connectivity as it connects to Southbridge 235 using both the Universal Serial Bus (USB) the PCI Express bus. Southbridge 235 includes USB Controller 240 that provides USB connectivity to devices that connect to the USB. These devices include webcam (camera) 250, infrared (IR) receiver 248, keyboard and trackpad 244, and Bluetooth device 246, which provides for wireless personal area networks (PANs). USB Controller 240 also provides USB connectivity to other miscellaneous USB connected devices 242, such as a mouse, removable nonvolatile storage device 245, modems, network cards, ISDN connectors, fax, printers, USB hubs, and many other types of USB connected devices. While removable nonvolatile storage device 245 is shown as a USB-connected device, removable nonvolatile storage device 245 could be connected using a different interface, such as a Firewire interface, etcetera.

Wireless Local Area Network (LAN) device 275 connects to Southbridge 235 via the PCI or PCI Express bus 272. LAN device 275 typically implements one of the IEEE 0.802.11 standards of over-the-air modulation techniques that all use the same protocol to wireless communicate between information handling system 200 and another computer system or device. Optical storage device 290 connects to Southbridge 235 using Serial ATA (SATA) bus 288. Serial ATA adapters and devices communicate over a high-speed serial link. The Serial ATA bus also connects Southbridge 235 to other forms of storage devices, such as hard disk drives. Audio circuitry 260, such as a sound card, connects to Southbridge 235 via bus 258. Audio circuitry 260 also provides functionality such as audio line-in and optical digital audio in port 262, optical digital output and headphone jack 264, internal speakers 266, and internal microphone 268. Ethernet controller 270 connects to Southbridge 235 using a bus, such as the PCI or PCI Express bus. Ethernet controller 270 connects information handling system 200 to a computer network, such as a Local Area Network (LAN), the Internet, and other public and private computer networks.

While FIG. 2 shows one information handling system, an information handling system may take many forms, some of which are shown in FIG. 1. For example, an information handling system may take the form of a desktop, server, portable, laptop, notebook, or other form factor computer or data processing system. In addition, an information handling system may take other form factors such as a personal digital assistant (PDA), a gaming device, ATM machine, a portable telephone device, a communication device or other devices that include a processor and memory.

Figure 3:
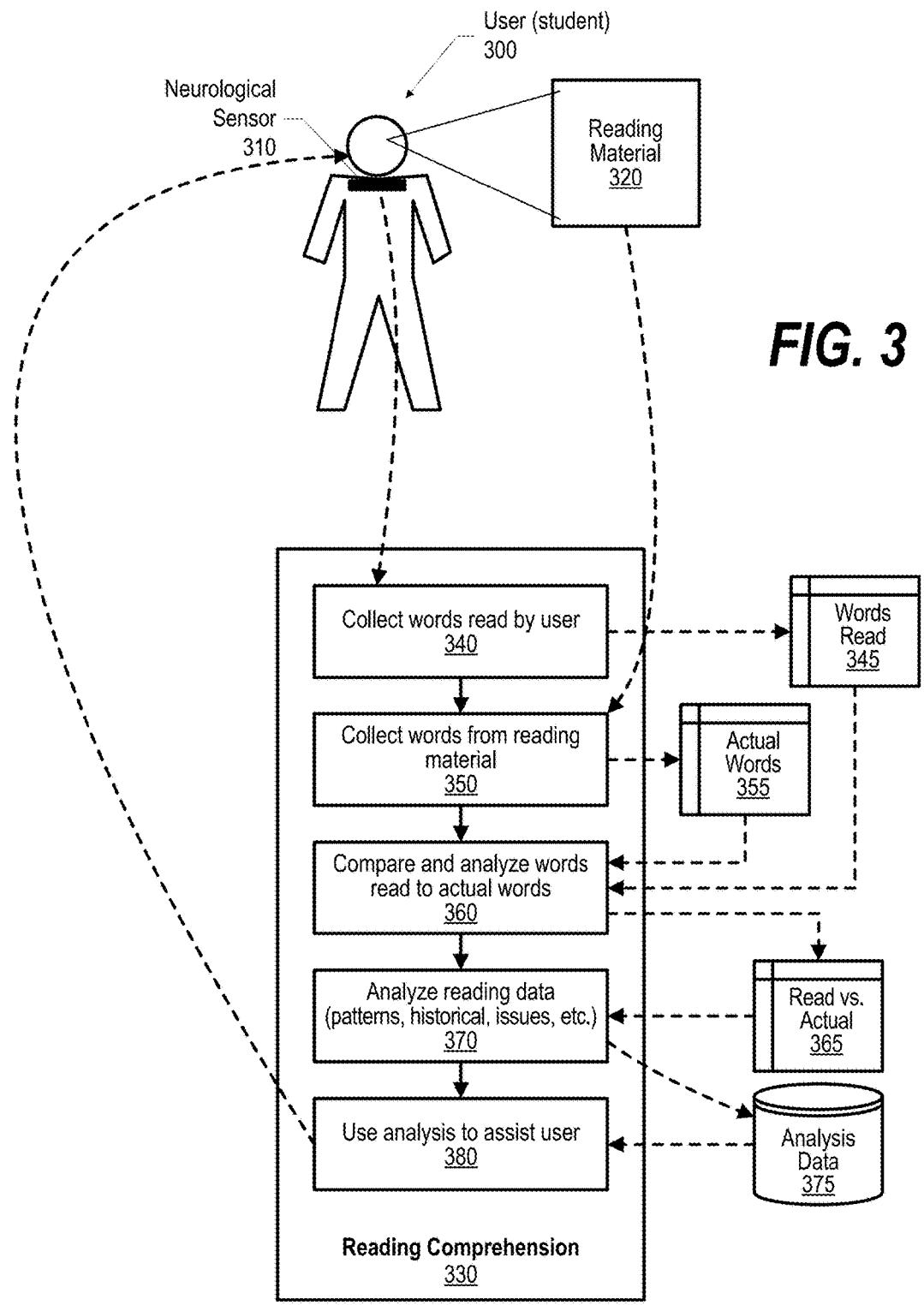
FIG. 3 is a component diagram that depicts interaction between a student wearing a neurological sensor and a reading comprehension application.

FIG. 3 is a component diagram that depicts interaction between a student wearing a neurological sensor and a reading comprehension application. User 300, such as a student or other person learning how to read or working to improve the user's reading ability, wears neurological sensor 310. In one embodiment, neurological sensor 310 is a device that is based on the idea that neurological signals sent from the user's brain to the throat area to initiate speech, such as occur during reading, still travel to the throat area even if the user does not audibly speak the words. Thus, even when the user does not audibly speak the words, the neurological signals that represent the intended speech exist when the user is reading. This is known as "sub-vocal speech," and is performed by user 300 whenever the user thinks, or reads, a word or sentence without saying it out loud. So, when user 300 reads a passage from reading material 320, the user's brain still sends the signals to the user's mouth and throat. These signals are captured by neurological sensor 310 from which reading comprehension system 330 gathers the words as read by the user.

Reading comprehension system 330 operates to gather reading data in order to analyze the data so that the user can be assisted, either directly or with use of a trained professional, such as a teacher, that reads the analysis data to assist user 300 with improved reading. Reading comprehension system 330 operates by performing a number of steps.

At step 340, the process collects words as read by user 300 as the user is reading passages from reading material 320. The words read by the user might not be the same as the actual words in the reading material. These differences, or mistakes, are identified and analyzed in order to assist the user. The words as read by the user are stored in memory area 345.

At step 350, the process collects the actual words from the passages included in reading material 320. Reading material 320 can be words of passages printed on hardcopy (paper), or displayed on a display screen. These are the actual words printed in the passages and not necessarily the words that were read by the user. The words in the passages can be already known to the system, or the words can be collected by traditional text collection techniques, such as by optical character recognition (OCR) tools or other known tools used to capture text either printed on paper or displayed on a display screen. Step 350 stores the actual words from the passages in memory area 355.

At step 360, the process compares and analyze the words as read by the user (retrieved from memory area 345) to the actual words from the passage (retrieved from memory area 355). Step 360 stores results from the comparison in memory area 365. In one embodiment, only mistakes made by the user are written to memory area 365 when a word read by the user does not match an actual word. In another embodiment, words correctly read by the user are also written to memory area 365 so that the user's improvements can be identified by noting those words that were correctly read in the current reading, but incorrectly read during previous readings.

At step 370, the process analyzes the reading data stored in memory area 365 and identifies any patterns, historical trends, reading issues/disabilities, and the like. The resulting analysis is stored in data store 375. At step 380, the process assists the user by providing the analysis written to data store 375 to user 300. The analysis can be provided directly to the user, or can be provided indirectly to the user by providing the analysis to a parent, guardian, or teacher or other professional who can then better assist the user in reading by utilizing the analysis data.

Figure 4:
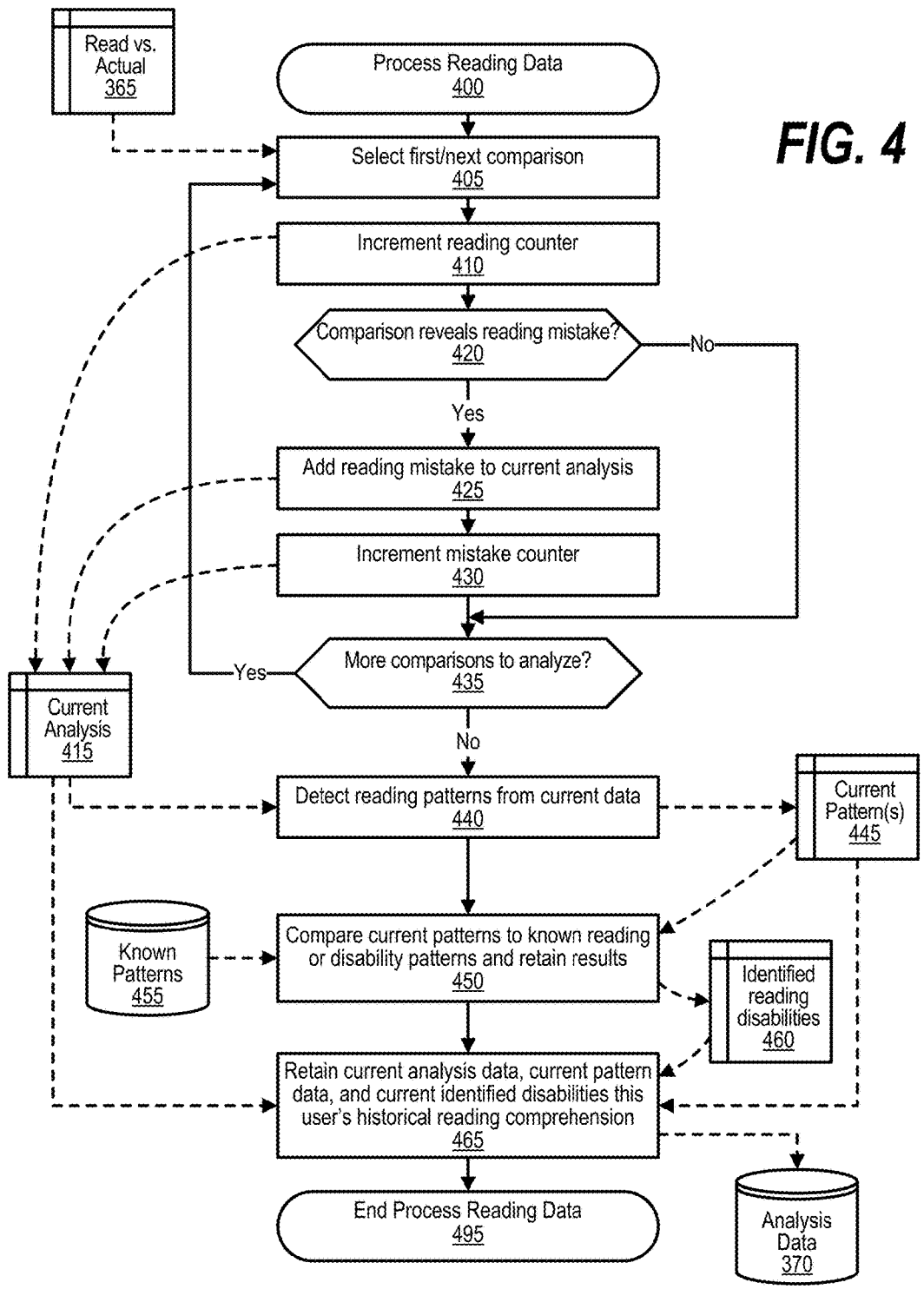
FIG. 4 is a depiction of a flowchart showing the logic used to process reading data gathered by the neurological sensor worn by students while reading.

FIG. 4 is a depiction of a flowchart showing the logic used to process reading data gathered by the neurological sensor worn by students while reading passages from a given set of reading material. FIG. 4 processing commences at 400 and shows the steps taken by a process that processes the reading data received from the neurological sensor that was worn by the user. At step 405, the process selects the first comparison from memory area 365 with the comparison being a word as read by the user and the actual word that was printed in the passage that was read by the user. At step 410, the process increments a reading counter and stores the incremented counter in memory area 415. The counter is used to count the number of words read by the user so that the system can determine a percentage of words that were correctly and incorrectly read by the user.

The process determines as to whether a comparison of the word as read by the user and the actual word reveals a reading mistake made by the user (decision 420). If the comparison reveals a reading mistake, then decision 420 branches to the 'yes' branch to gather data about the mistake. On the other hand, if no mistake was found, then decision 420 branches to the 'no' branch bypassing steps 425 and 430. In one embodiment, the process also writes correctly read words to current analysis memory area 415 so that words that used to be misread by the user but are now read correctly can be identified and such improvements noted in the current analysis of the user's reading performance.

If the comparison revealed a reading mistake, then steps 425 and 430 are performed. At step 425, the process adds the reading mistake to current analysis data that is stored in memory area 415. At step 430, the process increments a mistake counter that is used to keep track of the number of reading mistakes made by the user during the current, or latest, reading.

The process determines as to whether there are more comparisons in memory area 365 to select and analyze as described above (decision 435). If there are more comparisons to select and analyze, then decision 435 branches to the 'yes' branch which loops back to step 405 to select the next comparison from memory area 365 and analyzes the comparison as described above. This looping continues until there are no more words in memory area 365 to process, at which point decision 435 branches to the 'no' branch exiting the loop.

At step 440, the process detects reading patterns from current data. At step 450, the process compares the user's current patterns to known reading or disability patterns and retain results. In one embodiment, the patterns are compared by inputting the reader's current pattern data to a question-answering (QA) system such as QA system 100 shown in FIG. 1, with known patterns ingested from data store 455 to the corpus of QA system 100. In another embodiment, the user's current patterns are compared to known reading patterns by retrieving the known patterns from data store 455 and performing the comparisons. Any reading disabilities discovered by comparing the patterns are stored in memory area 460, such as a discovery that the user appears to suffer from dyslexia.

At step 465, the process retains the current analysis data from memory area 415, the current pattern data from memory area 445, and any currently identified disabilities from memory area 460 in this user's historical reading comprehension which is stored in data store 370. FIG. 4 processing thereafter ends at 495.

Figure 5:
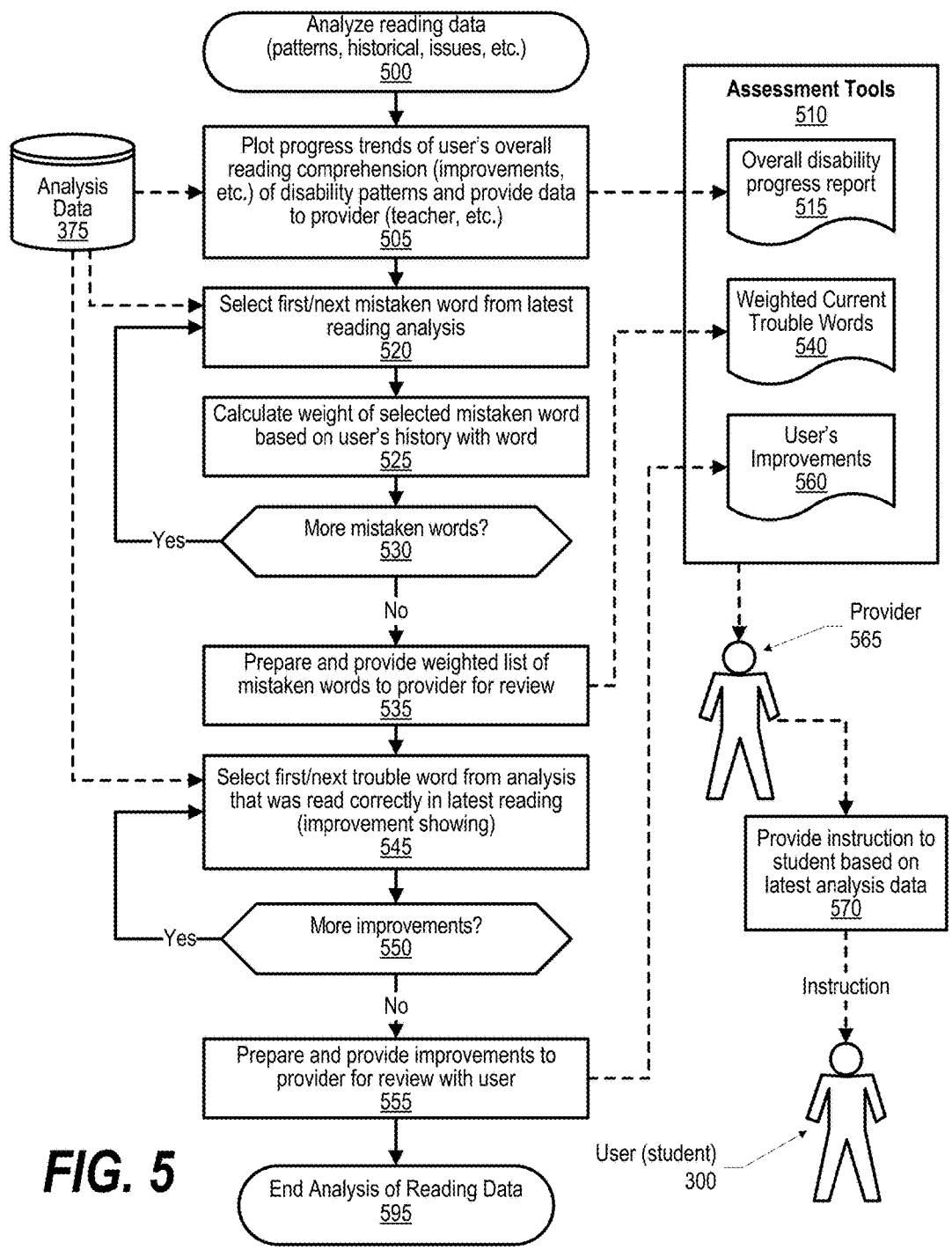
FIG. 5 is a depiction of a flowchart showing the logic used to analyze the reading data gathered for students using patterns, historical student learning data, and reading disability issues.

FIG. 5 is a depiction of a flowchart showing the logic used to analyze the reading data gathered for students using patterns, historical student learning data, and reading disability issues. FIG. 5 processing commences at 500 and shows the steps taken by a process that analyzes reading data with regard to any patterns identified, any historical trends, mistakes currently being made by the user during reading, and improvements identified as being made by the user. At step 505, the process plots the progress trends of the user's overall reading comprehension, such as challenges and improvements, and of the user's reading disability patterns detected. Step 505 retrieves the data from data store 375 and provides this data to the user or reading instructor (teacher, etc.) by storing the data in overall disability progress report 515.

At step 520, the process selects the first mistaken word from latest reading analysis with the mistakenly read word being retrieved from data store 375. At step 525, the process calculates a weight for the selected mistaken word based on the user's history with word. In one embodiment, words found to be repeatedly read incorrectly by the user are weighted more heavily so that such routinely troublesome words receive greater priority and emphasis during instruction time spent with the user. The process determines as to whether there are more mistaken words in data store 375 to select and weigh as described above (decision 530). If there are more mistaken words in data store 375 to select and weigh, then decision 530 branches to the 'yes' branch which loops back to step 520 to select and process the next mistakenly read word as described above. This looping continues until there are no more mistakes to process, at which point decision 530 branches to the 'no' branch exiting the loop. At step 535, the process prepares and provides a weighted, or prioritized, list of mistaken words to the user or the user's instructor (teacher, etc.) for review. The prioritized list of mistaken words is written to report 540, such as by reporting the mistakes in order from most troublesome words that are most often read incorrectly to those words that are least troublesome and not read incorrectly very often.

At step 545, the process selects the first historically troublesome word from analysis data 375 that was read correctly in latest the reading, but was incorrectly read during previous readings. This shows the improvement that the user is making with regard to reading certain words. The process determines as to whether there are more improvements noted in analysis data 375 (decision 550). If there are more improvements, then decision 550 branches to the 'yes' branch which loops back to step 545 to select the next improvement. This looping continues until all of the user's improvements have been processed, at which point decision 550 branches to the 'no' branch exiting the loop.

At step 555, the process prepares and provide an improvement report that is written to report 560. Improvement report 560, along with weighted current trouble words report 540 and overall disability progress report 515, are part of assessment tools 510 that are provided to user 300 or to instruction provider 565, such as a parent or teacher, to assist the user with their reading performance. If an instruction provider is being utilized then, at step 570, instruction provider 565 provides instruction to user 300 based on latest analysis data as set forth in assessment tools 510 If an instruction provider is not being utilized, then the assessment tools are provided directly to user 300, such as might be the case with an adult student that is learning a new language. FIG. 5 processing thereafter ends at 595.

While particular embodiments of the present invention have been shown and described, it will be obvious to those skilled in the art that, based upon the teachings herein, that changes and modifications may be made without departing from this invention and its broader aspects. Therefore, the appended claims are to encompass within their scope all such changes and modifications as are within the true spirit and scope of this invention. It will be understood by those with skill in the art that if a specific number of an introduced claim element is intended, such intent will be explicitly recited in the claim, and in the absence of such recitation no such limitation is present. For non-limiting example, as an aid to understanding, the following appended claims contain usage of the introductory phrases "at least one" and "one or more" to introduce claim elements. However, the use of such phrases should not be construed to imply that the introduction of a claim element by the indefinite articles "a" or "an" limits any particular claim containing such introduced claim element to inventions containing only one such element, even when the same claim includes the introductory phrases "one or more" or "at least one" and indefinite articles such as "a" or "an"; the same holds true for the use in the claims of definite articles.

What is claimed is:

1. A method implemented by an information handling system that includes a processor and a memory accessible by the processor, the method comprising:
    receiving, from a neurological sensor worn by a user, a plurality of words as read by the user, wherein the neurological sensor includes one or more electrode sensors attached to the user that capture electrical signals between the user's brain and the user's vocal cords, and wherein the plurality of words as read by the user correspond to a plurality of actual words included in a passage that is being silently read by the user, and wherein the plurality of words as read by the user and the actual words are stored in the memory;
    comparing, by the processor, the plurality of words as read by the user with the plurality of actual words included in the passage, wherein the comparing results in one or more identified mistakes;
    identifying a pattern from the identified mistakes;
    inputting the pattern to a question answering (QA) system with access to a corpus of currently known reading disability patterns;
    receiving, from the QA system, a matching reading disability corresponding to the identified pattern; and
    including the matching reading disability in a set of feedback that is provided to the user.

2. The method of claim 1 further comprising:
    selecting each of the mistakes, wherein each mistake includes a selected one of the words as read by the user and a selected one of the actual words;
    retrieving a set of historical data pertaining to each of the selected mistakes, wherein the set of historical data includes a plurality of past mistakes identified during one or more previous readings by the user;
    calculating a weight corresponding to each of the selected mistakes based on the retrieved set of historical data corresponding to each of the respective mistakes;
    prioritizing each of the selected mistakes based on each of the selected mistake's respective weight; and
    including the prioritized mistakes in the set of feedback that is provided to the user.

3. The method of claim 1 further comprising:
    identifying a plurality of correctly read words from the comparison of the plurality of words as read by the user with the plurality of actual words included in the passage;
    retrieving a set of historical data that includes a plurality of past mistakes identified during one or more previous readings by the user;
    matching one or more of the correctly read words with one or more past mistakes;
    preparing an improvement report based on the matching; and
    including the improvement report in the set of feedback that is provided to the user.

4. The method of claim 1 further comprising:
    selecting each of the mistakes, wherein each mistake includes a selected one of the words as read by the user and a selected one of the actual words;
    retrieving a set of historical data pertaining to each of the selected mistakes, wherein the set of historical data includes a plurality of past mistakes identified during one or more previous readings by the user;
    calculating a weight corresponding to each of the selected mistakes based on the retrieved set of historical data corresponding to each of the respective mistakes;
    prioritizing each of the selected mistakes based on each of the selected mistake's respective weight;
    identifying a plurality of correctly read words from the comparison of the plurality of words as read by the user with the plurality of actual words included in the passage;
    retrieving a set of historical data that includes a plurality of past mistakes identified during one or more previous readings by the user;
    matching one or more of the correctly read words with one or more past mistakes;
    preparing an improvement report based on the matching; and
    including the prioritized mistakes and the improvement report in the set of feedback that is provided to the user.

5. An information handling system comprising:
    one or more processors;
    a memory coupled to at least one of the processors; and
    a set of computer program instructions stored in the memory and executed by at least one of the processors in order to perform actions comprising:
        receiving, from a neurological sensor worn by a user, a plurality of words as read by the user, wherein the neurological sensor includes one or more electrode sensors attached to the user that capture electrical signals between the user's brain and the user's vocal cords, and wherein the plurality of words as read by the user correspond to a plurality of actual words included in a passage that is being silently read by the user, and wherein the plurality of words as read by the user and the actual words are stored in the memory;

comparing, by the processor, the plurality of words as read by the user with the plurality of actual words included in the passage, wherein the comparing results in one or more identified mistakes;

identifying a pattern from the identified mistakes;

inputting the pattern to a question answering (QA) system with access to a corpus of currently known reading disability patterns;

receiving, from the QA system, a matching reading disability corresponding to the identified pattern; and including the matching reading disability in a set of feedback that is provided to the user.

6. The information handling system of claim 5 wherein the actions further comprise:

selecting each of the mistakes, wherein each mistake includes a selected one of the words as read by the user and a selected one of the actual words;

retrieving a set of historical data pertaining to each of the selected mistakes, wherein the set of historical data includes a plurality of past mistakes identified during one or more previous readings by the user;

calculating a weight corresponding to each of the selected mistakes based on the retrieved set of historical data corresponding to each of the respective mistakes;

prioritizing each of the selected mistakes based on each of the selected mistake's respective weight; and including the prioritized mistakes in the set of feedback that is provided to the user.

7. The information handling system of claim 5 wherein the actions further comprise:

identifying a plurality of correctly read words from the comparison of the plurality of words as read by the user with the plurality of actual words included in the passage;

retrieving a set of historical data that includes a plurality of past mistakes identified during one or more previous readings by the user;

matching one or more of the correctly read words with one or more past mistakes;

preparing an improvement report based on the matching; and including the improvement report in the set of feedback that is provided to the user.

8. The information handling system of claim 5 wherein the actions further comprise:

selecting each of the mistakes, wherein each mistake includes a selected one of the words as read by the user and a selected one of the actual words;

retrieving a set of historical data pertaining to each of the selected mistakes, wherein the set of historical data includes a plurality of past mistakes identified during one or more previous readings by the user;

calculating a weight corresponding to each of the selected mistakes based on the retrieved set of historical data corresponding to each of the respective mistakes;

prioritizing each of the selected mistakes based on each of the selected mistake's respective weight;

identifying a plurality of correctly read words from the comparison of the plurality of words as read by the user with the plurality of actual words included in the passage;

retrieving a set of historical data that includes a plurality of past mistakes identified during one or more previous readings by the user;

matching one or more of the correctly read words with one or more past mistakes;

preparing an improvement report based on the matching; and including the prioritized mistakes and the improvement report in the set of feedback that is provided to the user.

9. A computer program product stored in a computer readable storage medium, comprising computer program code that, when executed by an information handling system, performs actions comprising:

receiving, from a neurological sensor worn by a user, a plurality of words as read by the user wherein the neurological sensor includes one or more electrode sensors attached to the user that capture electrical signals between the user's brain and the user's vocal cords, and, wherein the plurality of words as read by the user correspond to a plurality of actual words included in a passage that is being silently read by the user, and wherein the plurality of words as read by the user and the actual words are stored in the memory;

comparing, by the processor, the plurality of words as read by the user with the plurality of actual words included in the passage, wherein the comparing results in one or more identified mistakes;

identifying a pattern from the identified mistakes;

inputting the pattern to a question answering (QA) system with access to a corpus of currently known reading disability patterns;

receiving, from the QA system, a matching reading disability corresponding to the identified pattern; and including the matching reading disability in a set of feedback that is provided to the user.

10. The computer program product of claim 9 wherein the actions further comprise:

selecting each of the mistakes, wherein each mistake includes a selected one of the words as read by the user and a selected one of the actual words;

retrieving a set of historical data pertaining to each of the selected mistakes, wherein the set of historical data includes a plurality of past mistakes identified during one or more previous readings by the user;

calculating a weight corresponding to each of the selected mistakes based on the retrieved set of historical data corresponding to each of the respective mistakes;

prioritizing each of the selected mistakes based on each of the selected mistake's respective weight; and including the prioritized mistakes in the set of feedback that is provided to the user.

11. The computer program product of claim 9 wherein the actions further comprise:

identifying a plurality of correctly read words from the comparison of the plurality of words as read by the user with the plurality of actual words included in the passage;

retrieving a set of historical data that includes a plurality of past mistakes identified during one or more previous readings by the user;

matching one or more of the correctly read words with one or more past mistakes;

preparing an improvement report based on the matching; and including the improvement report in the set of feedback that is provided to the user.

12. The computer program product of claim 9 wherein the actions further comprise:

selecting each of the mistakes, wherein each mistake includes a selected one of the words as read by the user and a selected one of the actual words;

retrieving a set of historical data pertaining to each of the selected mistakes, wherein the set of historical data includes a plurality of past mistakes identified during one or more previous readings by the user;

calculating a weight corresponding to each of the selected mistakes based on the retrieved set of historical data corresponding to each of the respective mistakes;

prioritizing each of the selected mistakes based on each of the selected mistake's respective weight;

identifying a plurality of correctly read words from the comparison of the plurality of words as read by the user with the plurality of actual words included in the passage;

retrieving a set of historical data that includes a plurality of past mistakes identified during one or more previous readings by the user;

matching one or more of the correctly read words with one or more past mistakes;

preparing an improvement report based on the matching; and including the prioritized mistakes and the improvement report in the set of feedback that is provided to the user.

* * * * *